United States Patent [19]

Ash

[11] Patent Number: 4,661,246
[45] Date of Patent: Apr. 28, 1987

[54] DIALYSIS INSTRUMENT WITH DIALYSATE SIDE PUMP FOR MOVING BODY FLUIDS

[75] Inventor: Stephen R. Ash, Lafayette, Ind.

[73] Assignee: Ash Medical Systems, Inc., West Lafayette, Ind.

[21] Appl. No.: 656,314

[22] Filed: Oct. 1, 1984

[51] Int. Cl.$^4$ .................... B01D 13/00; A61M 1/16
[52] U.S. Cl. ........................... 210/87; 210/94; 210/110; 210/134; 210/195.2; 210/257.2; 210/266; 210/295; 210/321.3
[58] Field of Search ............ 210/87, 94, 110, 134, 210/189, 195.2, 257.2, 266, 295, 321.2, 321.3; 604/67

[56] References Cited

U.S. PATENT DOCUMENTS

| | | | |
|---|---|---|---|
| 3,570,672 | 3/1971 | Bach | 210/110 |
| 3,774,762 | 11/1973 | Lichtenstein | 210/321.3 X |
| 3,902,490 | 9/1975 | Jacobsen et al. | 210/321.3 |
| 3,962,075 | 6/1976 | Fialkoff et al. | 210/321.3 X |
| 3,989,625 | 11/1976 | Mason | 210/321.3 X |
| 4,071,444 | 1/1978 | Ash et al. | 210/321 X |
| 4,118,314 | 10/1978 | Yoshida | 210/321.3 |
| 4,231,366 | 11/1980 | Schael | 604/67 X |
| 4,267,041 | 5/1981 | Schael | 210/321.3 X |
| 4,348,283 | 9/1982 | Ash | 210/321.3 |

Primary Examiner—Richard V. Fisher
Assistant Examiner—W. Gary Jones
Attorney, Agent, or Firm—Woodard, Weikart, Emhardt & Naughton

[57] ABSTRACT

A dialysis instrument having a pump located on the dialysate side of a dialyzer for moving body fluids. A disposable cartridge mounted to a main frame includes containers of calcium chloride, priming solution, water, sorbent column, dialysate reservoir bag and potassium/hydrogen citrate reinfusate reservoir. A plurality of monitors detect the status of the flow of fluids and process of dialysis and provide data for the operation of a plurality of pumps and clamps to control the direction of flow of various fluids. The entire instrument is mounted on a scale to detect weight change due to the difference between inflow and outflow of body fluids.

13 Claims, 6 Drawing Figures

DIALYSIS INSTRUMENT WITH DIALYSATE SIDE PUMP FOR MOVING BODY FLUIDS

BACKGROUND OF THE INVENTION

1. Field of the Invention

This invention is in the field of medical instruments for processing body fluids including an instrument to perform hemodialysis.

2. Description of the Prior Art

The usual approach to performance of single access dialysis is to pump blood into the dialyzer by a roller pump on the arterial or inflow blood tubing. The venous limb has an air-filled tubing leading to a pressure gauge and a downstream clamp. The reading of the pressure gauge is the controller of the flow into the dialyzer, and the volume in the dialyzer. On inflow of blood to the dialyzer, the venous limb is clamped, the blood pump started, and the blood volume and pressure increase in the dialyzer and venous drip chamber. The relationship of pressure to the volume in the dialyzer is determined by the "compliance" or "stiffness" of the dialyzer. On outflow, the roller pump is stopped, and the venous clamp opened. The discharge of blood is entirely "passive." The volume in the dialyzer and drip chamber decrease. The degree of emptying of the dialyzer is indicated by the pressure fall at the venous drip chamber. The same relationship of pressure to volume in the dialyzer is dictated by the "compliance" curve for the dialyzer. The venous drip chamber itself acts as a significant "accumulator." In use of hollow fiber dialysis, the patient or nurse must watch to make sure that the air-blood lever in the drip chamber does not expand out of the chamber into the exiting tube and travel toward the patient. Alternatively, an ultrasound or optical monitor may be used to monitor the level of blood in the drip chamber. If an arterial drip chamber is used to monitor the pressure on the inflow tube to the dialyzer (to measure resistance or clotting of the dialyzer), the air-blood interface on the chamber must also be monitored. In short, the operation of a standard "single access" adapter to a dialysis system adds to the complexity of dialysis. Partly for this reason, single access dialysis is rarely used for home dialysis.

In the system disclosed herein, the blood volume in the dialyzer is also related to pressure in the dialyzer by the compliance curve. However, rather than measuring the fullness of the dialyzer by changes in pressure in the venous drip chamber, the system measures the rate flow into and out of the dialyzer directly.

A commercially available plate dialyzer is used (Cobe 1.6M2), with know compliance curves. Two optical flow meters are used, one on the inflow (arterial) blood tubing, and one on the outflow (venous) blood tubing. The optical sensors measure the flow of blood and abnormal particle content. As the dialyzer fills, the internal pressure increases and the rate of inflowing blood diminishes. The dialyzer empties passively. The rate of flow diminishes as the blood volume within the dialyzer diminishes. The degree of filling and emptying of the dialyzer and blood flow are optimized through flow monitoring as well as by the older method of measurement of the venous drip chamber pressure.

With PVC tubing, a standard roller pump has a maximal negative pressure (about −450 mm Hg) and a positive pressure achievable of over 1000 mm Hg. Thus, an arterial roller pump, such as used in the prior dialysis instruments, can exert a highly negative pressure on a fistula needle or catheter, in the case of blockage or venous collapse. Without an "arterial" drip chamber and pressure monitor, a clotted dialyzer in front of the pump can receive very high positive pressure. The system disclosed herein uses a roller pump on the outflow dialysate tube to expand dialyzer membranes and move blood into the dialyzer. Thus, the transmembrane pressure is substracted from the maximum negative pressure created by the roller pump, diminishing this pressure by 100-200 mm Hg. Furthermore, the maximal forward pressure cannot be delivered to the dialyzer, but only to the dialysis side components. In addition, the dialyzer membranes dampen some of the variations in flow providing a smoother flow of blood into the dialyzer.

In my U.S. Pat. Nos. 4,071,444 and 4,348,283 I have disclosed reciprocating dialyzers using a sorbent suspension. Another dialysis machine is available from Drake Willock under model number 8806/8805/8802 and is similar to the system disclosed herein in that single needle dialysis is performed by controlling the blood flow alternately into and out of a single needle veni-puncture; however, the Drake Willock model requires use of a venous drip chamber unlike my system and further utilizes a blood pump in lieu of a dialysate pump. Another commercially available dialysis machine is Organon Teknika Sorbsystem model SS-D which also utilizes a blood side pump with either a two needle access or single needle access. The number and quantity of disposables used with a dialysis instrument necessitates in the prior art devices considerable attention by the operator to insure proper usage. The system disclosed herein is provided with a removable cartridge which may be discarded containing all of the disposables needed for multiple dialysis treatments. The system utilizes a dialysate-side pumping mechanism for providing single needle dialysis. Thus, the system is more adaptable for use at home since the user may simply mount a fresh cartridge for dialysis, and remove and discard the cartridge at the end of each dialysis treatment.

SUMMARY OF THE INVENTION

One embodiment of the present invention is a single access dialysis instrument comprising a single catheter for receiving body liquids, a dialyzer having a body liquid side with fluid inlet and fluid outlet connected to the catheter and further having a dialysate side with a dialysate inlet and a dialysate outlet, storage means connected to the dialysate inlet and the dialysate outlet and operable to hold a supply of liquid including dialysate for use in the dialyzer, pumping means connected to the dialysate side of the dialyzer and operable to directly apply fluid withdrawal pressure to the dialysate outlet resulting in pressure at the fluid inlet to cause fluid flow into the dialyzer through the fluid inlet.

Another embodiment of the present invention is a monitor for detecting ammonium in a fluid comprising a tube to convey fluid with the tube having an outlet to allow ammonia gas to escape therethrough, a gas permeable membrane extending across the outlet, a test strip positioned adjacent the membrane and including reacting chemicals to react with ammonium and change color in the process, and color detecting means positioned adjacent the strip operable to detect changes in color in the strip.

Yet another embodiment of the present invention is a dialysis instrument comprising a catheter for receiving body liquids, a dialyzer having a body liquid side with fluid inlet and fluid outlet connected to the catheter and further having a dialysate side with a dialysate inlet and a dialysate outlet, a dialysate reservoir container for holding a quantity of dialysate and having an outflow port connected to the dialysate inlet and an inflow port connected to the dialysate outlet, a reinfusate reservoir having citrate therein being in fluid communication with the dialysate reservoir to supply the citrate into the dialysate for the replenishment thereof, pumping means connected to the dialyzer and operable to cause fluid flow into the dialyzer through the fluid inlet from the catheter.

It is an object of the present invention to provide a new and improved dialysis instrument.

Yet another object of the present invention is to provide a dialysis instrument having a pump located on the dialysate side of the dialyzer for moving body fluids into the dialyzer on the opposite side.

Yet another object of the present invention is to provide dialysis instrument providing a smoother inflow of blood.

In addition, it is an object of the present invention to provide a user operated dialysis instrument having interchangeable cartridges containing all required disposables and fluids.

A further object of the present invention is to provide an improved ammonium monitor which continuously operates without leaching and with a single disposable strip.

An object of the present invention is to provide a dialysis instrument with means for replenishing citrate in the dialysate. In addition, it is an object to use the citrate as an anti-coagulant replacing heparin as an anti-coagulant.

Related objects and advantages of the present invention will be apparent from the following description.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being comtemplated as would normally occur to one skilled in the art to which the invention relates.

Figure 1:
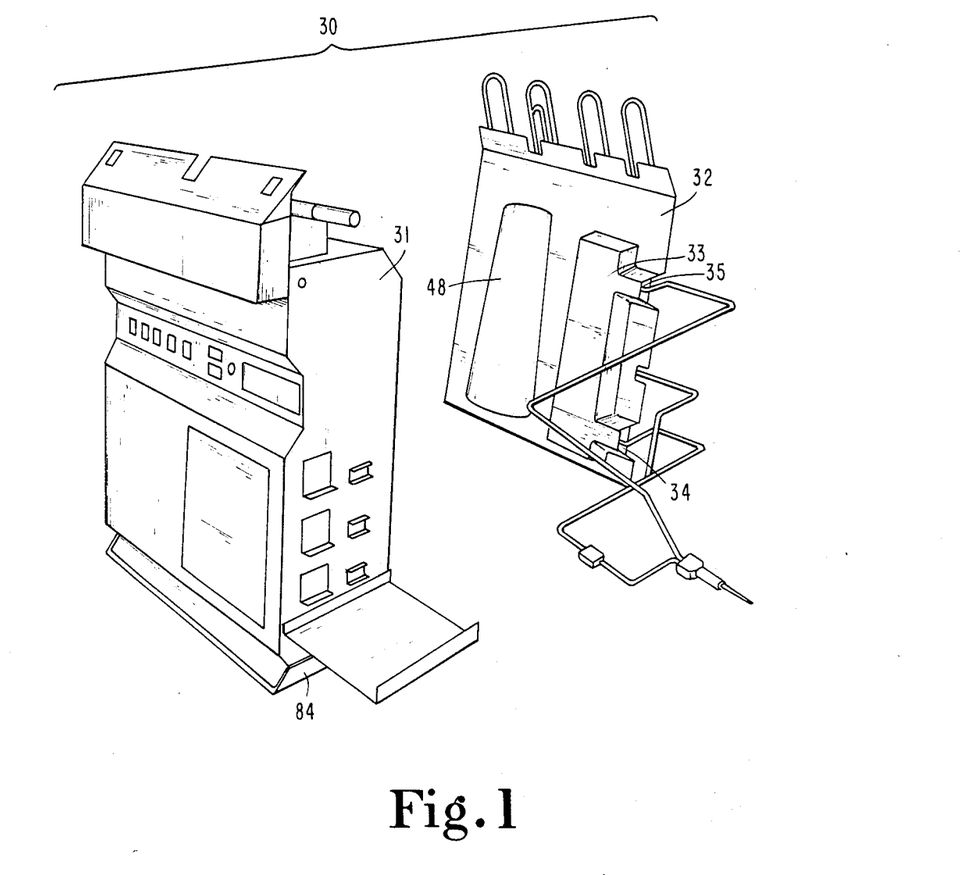
FIG. 1 is an exploded perspective view of the preferred embodiment of the dialysis instrument incorporating the present invention and showing the main frame and disposable cartridge.

Referring now more particularly to FIG. 1, there is shown a dialysis instrument 30 which is a computer controlled, flow monitored, battery operated machine for removing biologic fluid from the body, treating it and returning it to the body. Instrument 30 includes a main frame 31 with a disposable cartridge 32 mounted thereto. Conventional means may be utilized to secure the cartridge so long as the cartridge is easily removable by the user. Instrument 30 may be used to perform hemodialysis through a single venous catheter such as a fistula catheter. The hemodialysis treatment can be achieved with maximum simplicity, safety and mobility with the average dialysis patient being able to perform hemodialysis by himself in a self care unit or at home.

Figure 2:
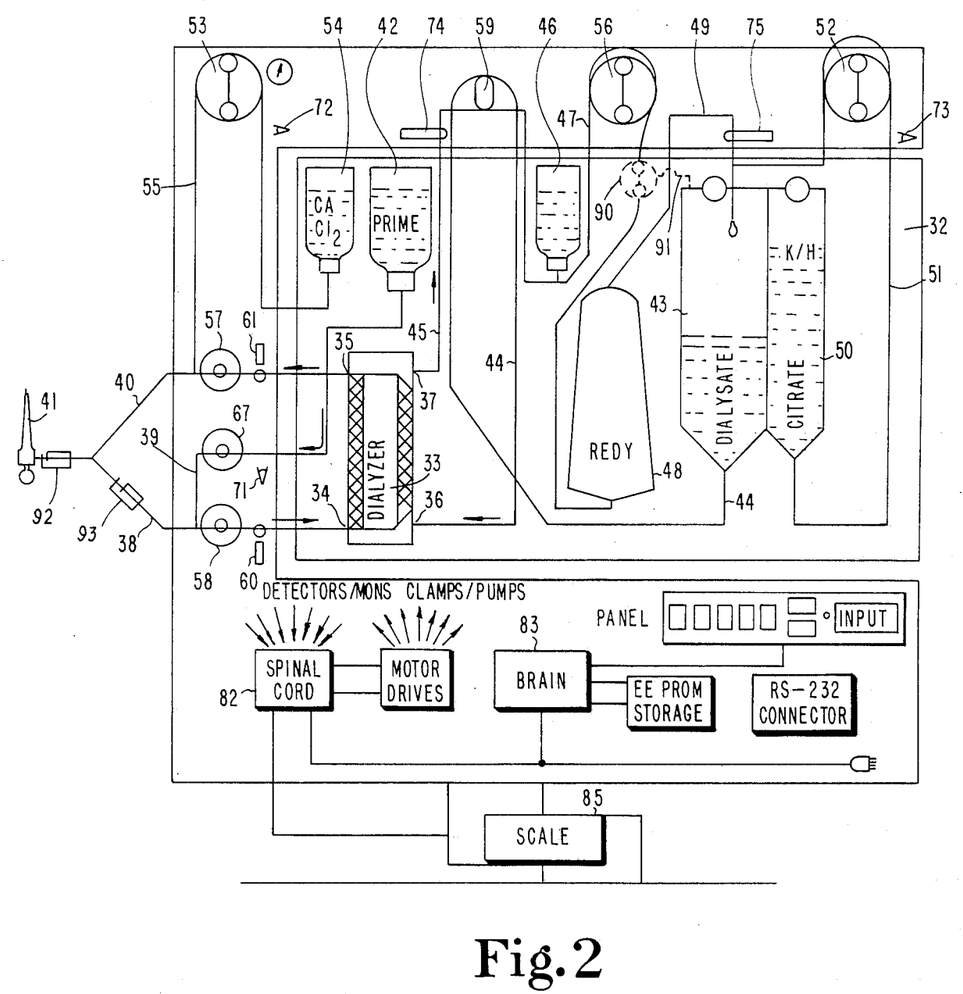
FIG. 2 is a schematic diagram showing the dialyzer connected via tubing to the containers with disposables therein along with the associated pumps, clamps and monitors.

FIG. 2 is a schematic diagram showing various containers having the disposables therein as well as depicting the dialyzer, pumps, clamps and monitors. Disposable cartridge 32 includes a commercially available Cobe 1.6M2 plate dialyzer 33 having a blood inlet 34, blood outlet 35, a dialysate inlet 36 and dialysate outlet 37, and a column 48 for regeneration of dialysate (Organon Teknika Hisorb). Column 48 contains the following layers: Urease, H-NA zirconium phosphate, acetate-zirconium oxide, and charcoal. The cartridge 32 provides ease of set up and breakdown and for the first time complete disposal of dialysate and blood side components with each use. Since the dialysis system is sorbent based, the dialysis procedure may be performed at any location using only 3.3 liters of potable tap water. The battery on the machine, and its low overall weight allow mobility for up to one-half hour during dialysis.

Three blood side tubes 38–40 are attached to the disposable cartridge. Tube 38 is an inflow or arterial blood tube connected to and between catheter 41 and the blood inlet 34 of the dialyzer. Tube 40 is the outflow or venous tubing leading from blood outlet 35 to catheter 41. Tube 39 is connected to and between the inflow tube 38 and container 42 having a prime and flush solution (5% Dextrose). Arrows are drawn next to tubes 38–40 to show the direction of the flow.

A six liter capacity ultrafiltrate reservoir 43 is mounted on the disposable cartridge along with the prime and flush solution in container 42. The outlet of reservoir 43 is connected via tube 44 to the dialysate inlet 36 of dialyzer 33. The dialysate outlet 37 of the dialyzer is connected via tube 45 to a vacuum accumulator container 46 in turn connected via tube 47 to the inlet of the Organon HiSorb Sorbent column 48. The HiSorb column 48 is mounted to the cartridge and allows enough ammonia absorbing capacity for 30 grams nitrogen. This absorption is equivalent to a drop in BUN from 100 mg% to 25 mg% for a 70 kg patient with 40 liters total body water. Since the disposable cartridge is a unitary package which does not allow replacement of the column, or any other component, even the blood side priming solution (one liter 5% dextrose) is included and is shown as container 42. The outlet of column 48 is connected via tube 49 to the inlet of reservoir 43. A reinfusate reservoir 50 is mounted to the disposable cartridge and contains hydrogen or potassium citrates and has an outlet connected to tube 51 leading to infusate pump 52 in turn connected to tube 49 to continually put potassium and citrate into the dialysate. The transfer of citrate from dialysate to blood may allow heparinless dialysis in some patients, should diminish heparin requirements in all patients, and improve biocompatibility of the dialyzer. The reinfusate reservoir 50 contains a combination of hydrogen and potassium citrates to produce effective dialysate potassium concentrations of about 1, 2 or 3 mEq/L. The citrate delivery to the dialysate is approximately 3 meq/min, an outflow blood concentrations of about 2 mg/L. A second pump 53 is operable to force five percent calcium chloride from container 54 mounted to the disposable cartridge through tube 55 in turn connected to the blood outflow tube 40 thereby returning five percent calcium chloride to the outflow blood, to replace calcium removed by the dialysate which has a calcium concentration of zero.

DIALYZER OPERATION

The dialysate roller pump 56 is operable to pull dialysate through tube 47 and in turn from the dialysate outlet 37 via tube 45 with the dialysate flowing in the direction of the arrows shown on tube 45. Tube 45 has a relatively large inside diameter to aid flow from the dialyzer. Thus, the pump is located on the dialysate side of dialyzer 33. During blood inflow, clamp 57 on the outflow blood tube 40 is closed, and the inflow blood clamp 58 is opened. Simultaneously, clamp 59 on the inflowing dialysate tube 44 is closed, and roller pump 56 continues to apply pumping pressure to the outflow (top) dialysis tube 45. The pump 56 operates at all times during the dialysis. A water container 46 is provided on tube 47 providing a build up of negative pressure by operation of pump 56 whenever tube 44 is closed by clamp 59. Thus, upon opening of tube 44, a negative pressure is quickly applied by container 46 to the outlet 37 until the pressure is maintained by pump 56. An optical flow meter 60 monitors the flow in the inflowing blood tube 38 continuously. At the start of the inflow, the blood flow rate increases rapidly, as the pressure decreases in the dialysate side of the membrane within dialyzer 33. As the dialyzer continues to fill with blood, the rate then falls off. At this point, there is a dissociation between the speed of the dialysate side pump, and the blood flow. This dissociation is due to partial collapse of the tubing in the dialysate roller pump, and also to expansion of small air bubbles within the dialyzer itself. The degree of dimution of inflowing blood rate is related to the filling of the dialyzer. The higher the fill volume, the lower the flow rate into it. This relationship can be used as an accurate indication of the point at which the dialyzer is satisfactorily full of blood. The further the filling of the dialyzer, the higher the transmembrane pressure. A computer monitors the inflowing blood rate at intervals of 1 millisecond. At a level determined by the computer, adjusted to provide an adequate ultrafiltration rate, inflow is ended and outflow portion of the cycle is begun.

During outflow, clamp 57 on the outflow blood line is opened, the inflow clamp 58 is closed, and the inflow dialysate line 59 clamp is simultaneously opened. The negative pressure which has built up in the dialyzer case draws in the dialysate from the reservoir bag 43. On the blood side, the pressure in the dialyzer diminishes, as blood flows out of the dialyzer, and volume in the dialyzer decreases. At all times there is a positive gradient of pressure from blood to dialysate. The flow rate of blood during outflow first increases and then decreases, as the volume in the dialyzer and the pressure on the blood side diminish. At a preset outflow flow rate, determined by the computer, the outflow is ended. At this point, the outflowing blood line is clamped, the inflow blood line is opened, and the inflow dialysate tube 44 is closed. The next inflow cycle begins.

Widespread optical and chemical sensors monitor the blood flow, fluid levels, particles and bubbles contamination, and chemical process of the dialysis.

BLOOD FLOW OPTICAL DETECTORS

Two optical monitors are provided on the inflow and outflow blood tubing. These monitors serve to indicate the degree of emptying or filling of the hemodialyzer membranes. A second function of these monitors is to detect the passage of small bubbles, air fluid interfaces, and micro aggregates within the blood.

Monitor 60 mounted to tube 38 will now be described, it being understood that an identical description applies to monitor 61 mounted to tube 40. Optical monitor 60 (FIG. 3) uses an incident tungsten light 62 directed at 90 degrees to the flow of blood and illuminating the blood through the surrounding blood tubing 63. The tubing 63 is compressed, just under the incident light, to affix it in place, and to create a thin blood channel of about 1 millimeter thickness. This thin blood channel allows closer inspection of blood, and better transmission of the light. On the opposite side of tungston light 62 are two receiving sensor phototransistors 64 and 65. With the passage of the red cells and collections of red cells, interruptions in the light are measured by the primary phototransistors 64 and 65 opposite the LED. The output of these phototransistor is a voltage, which is then analyzed to determine the frequency variation. As the speed of blood increases, the interruptions of the light occur faster, and the frequency of the signal increases. With diminished flow, the frequency of the signal diminishes.

Figure 3:
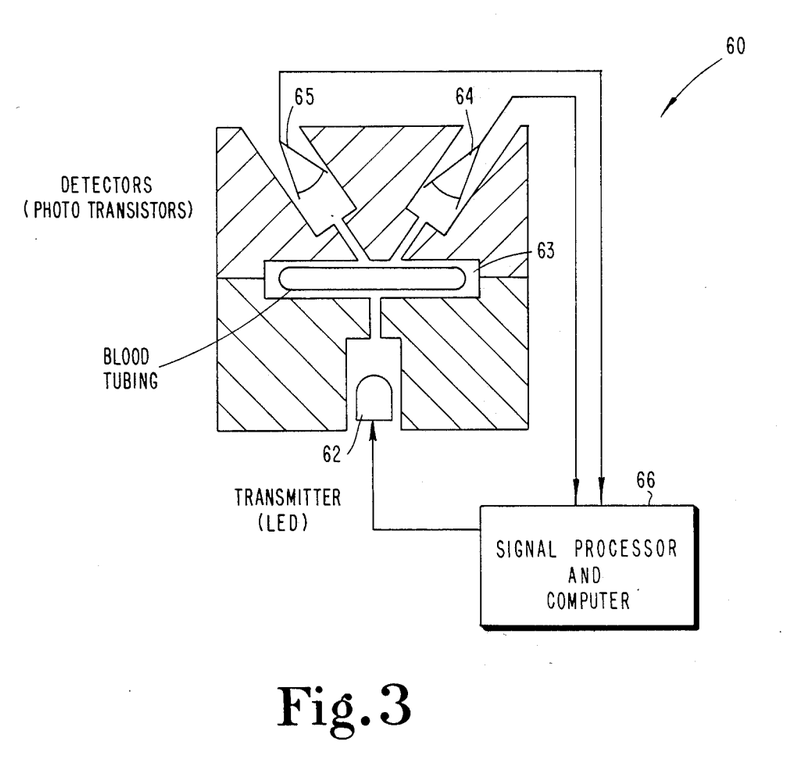
FIG. 3 is a schematic diagram of the blood flow optical detector.

The phototransistors 64 and 65 also pick up light reflected or "scattered" particles. The intensity of this reflected light is related to the number and size of the particles. Very small bubbles (0.1 mm size or so) produce bright, brief reflections. The intrinsic frequency of these signals is much higher than than produced by blood flow. Platelet aggregates, red cell aggregates, or clots produce reflections of frequency less than bubbles, and more than that of blood flow. An air-fluid interface produces a very strong reflection, with subsequent loss of blood flow signal. The signal processor of computer 66 contains filters which separate the output of the phototransistor into signals related to blood flow (low frequency), clots (middle frequency) and bubbles (high frequency).

The intensity of the reflected light (recorded at the primary phototransistor) is related to the hematocrit of the blood. Dialysis patients have a wide range of hematocrits, depending upon their degree of anemia (usually, from 15–40% packed cell volume). During a hemodialysis treatment, the hematocrit changes, as fluid is ultrafiltered from the patient's blood. In order to correct for variations and changes in hematocrit, and provide adequate transmitted and reflected light for sensing, there is a feedback circuit including a signal processor and computer 66 between the phototransistors and the LED. This circuit adjusts the power to the LED to give an adequate and constant output from the primary phototransistor. When the hematocrit is excessively low, 3% or less, the circuit is unable to increase the LED output enough to monitor an adequate signal. This property is useful to indicate the end point of rinsing of the dialyzer. The outflow monitor 61 indicates a very low hematocrit. At this time, rinsing is terminated. If, at the beginning of hemodialysis, a signal cannot be recorded from the primary phototransistor 64, then this indicates to the computer that the LED or the phototransistor is malfunctioning.

PRIMING

Before dialysis, the blood side of the Disposables Cartridge 32 is filled with the priming solution. The optical monitors 60 and 61 do not record priming solution flow since the clear priming solution does not contain particles to reflect light to the phototransistors. The control of the inflow and outflow of the dialyzer during PRIME mode is by pre-set timing of the dialysate side clamp 59. Upon initiation of the prime mode, manual clamp 92 is closed, clamp 93 is left open, electric clamps 58 and 67 opened, and clamp 57 closed. This allows the 5% detrose solution in container 42 to flow into dialyzer 33. The electric clamp 59 closes line 44, opens line 45 and the roller pump 56 removes dialysate from the dialyzer 33. Clamp 57 is then opened, clamp 58 is closed, and clamp 59 closes line 45 and opens line 44, allowing dialysate to enter dialyzer 33 and the primary solution to flow out of dialyzer 33 and back into container 42 via tubes 40, 38 and 39. During this time, the optical monitor 60 detects the passage of an air-fluid interface into the dialyzer. Monitor 61 detects an air fluid interface, then detects bubbles, as the priming solution replaces the air in the dialyzer and exits from the dialyzer. The successive signals of air-fluid interfaces from the monitors 60 and 61 during PRIME further indicates the proper functioning of the monitors. The circulation of priming solution from container 42 via tubes 39 and 38 into and out of dialyzer 33 continues until the monitor 61 indicates the passage of 0 bubbles or particles in each minute of operation. At the end of the priming procedure, the manual clamp 92 is opened momentarily, to fill needle 41 with blood.

At beginning of dialysis, blood enters tube 38. The phototransistors of optical monitor 60 thus begin to receive reflected light, the frequency of which indicates the flow of blood, as it increases, then decreases as the dialyzer fills. After one or two cycles, blood begins to leave the dialyzer. The recorded flow rate from each flow monitor further indicates the proper operation of the monitors, and this signal is used to control of the flow into and out of the dialyzer during the rest of the dialysis.

During dialysis, the monitors continually monitor for flow and particulate content of the blood. Signals indicating flow (low frequency signal of the phototransistors) bubble content (changes in high frequency signal of the phototransistors) and clot content (middle frequency signals of the phototransistors) are continuously available to the computer. The computer samples these signals at a rapid rate. The flow data is used to indicate the degree of filling and emptying of the dialyzer. Any signal indicating presence of impurities causes the computer to close all clamps immediately, and the machine to enter the ALARM condition. The clamps close in 0.1 seconds. At a maximal blood flow rate of 300 ml/min, only 0.5 ml of blood passes optical monitor, before the clamps are closed. In tubings 38 and 40, this represents a distance of only 2.5 cm. Thus, a particle passing the monitor 61 would be prevented from entering the fistula or fistula needle 41, by the monitor and the ALARM condition of the machine.

At the end of dialysis, the RINSE mode of operation is used to flush blood from the dialyzer by opening clamps 67 and 58 on tubes 39 and 38. The low frequency (flow) output of monitors 60 and 61 eventually ceases as the passage of clear fluid replaces blood flowing into and out of the dialyzer. When the outflow monitor rate indication ceases, then RINSE is ended, and the machine goes into PAUSE. The level of hematocrit in the outflow blood is approximately 3–6% at this time. Thus, monitor 61 serves to indicate the adequacy of rinsing of the dialyzer, preventing excessive retention of blood by the dialyzer, or excessive return of priming fluid to the patient.

AIR-FLUID INTERFACE DETECTORS

The fluids supplied with Disposables Cartridge 32, and the volumes of water added before dialysis, should be sufficient for operation through any standard dialysis treatment. It is possible, though unlikely, that a leak could occur at a connection, or that the fluids would be depleted during dialysis, or that the patient would forget to add water to one of the compartments. For this reason, back up sensors exist at various locations in the system. Three sensors 71, 72 and 73 detect the passage of an air-fluid interface in the tubing connected to one of the following containers: priming solution 42, calcium chloride solution 54, and K/H Citrate 50. While there is no fluid level indicator for the ultrafiltrate reservoir 43, if insufficient water is added to this compartment, the adverse effects of this deficiency will be readily apparent. Water will not fill the dialysate side of the dialyzer and the sorbent cartridge. The continued presence of air in the dialyzer will now allow the system to pump priming solution or blood through the dialyzer at the desired rates. This low flow rate will be detected by the slowness of passage of air-fluid interfaces past the optical blood flow monitors.

Figure 4:
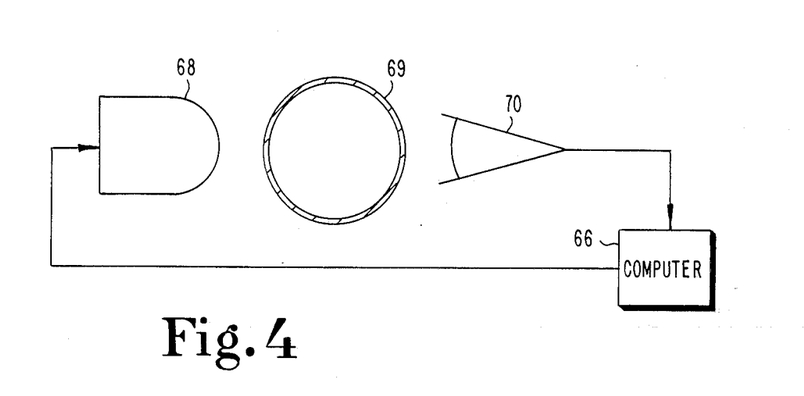
FIG. 4 is a schematic diagram of the air-fluid interface detectors.

The air-fluid interface detectors are optical devices as are the flow/particle monitors. FIG. 4 indicates the major components of these detectors 71–73. An infrared light emitting diode 68 shines light through the tubing 69 containing the fluid of interest. A receiving phototransistor 70 produces a voltage output proportional to the light it receives. During the CHECK/INPUT mode, the output of the phototransistor 70 is checked. An adequate output indicates proper operation of both the LED 68 and phototransistor 70. During operation of the machine, the output of the phototransistor is checked at a frequency of 10 Hz, by the computer 66.

The LED 68 is turned off and on intermittently, under computer control, with a longer off period than on. Turning the LED off is advantageous for several reasons. First, it allows easy correction for the effect of ambient light on the phototransistor output 70. Secondly, since the LED is only on for short periods of time, the LED will not heat up, which can result in a change of output. Third, the useful lifetime of the LED is increased.

During the PRIME mode the operation of the roller pumps and clamps propels fluid through the blood and dialysate sides of the disposables. Pumps 52 and 53 are operated at a flow rate higher than that used in the DIALYZE mode, to allow rapid filling of the tubing connecting them to the rest of the disposables. Tachometers on these pumps feed back the actual speed of the pumps to the computer. The higher speed allows the tubing segments to be filled early in the PRIME mode, and a shorter total PRIME time.

As fluid (water) displaces the air in the tubes 55 and 51, an air-fluid interface approaches each interface detector 72 and 73. This interface, like the surface of a bubble, tends to reflect or bend light. When the interface reaches a point just under the LED, the intensity of light reaching the phototransistor is diminished. The computer is programmed to expect the passage of this interface, at a certain time (calculated from the length of the tubing segment, and the pump flow rate). The high pump flow rate then continues for the amount of time expected to fill the remainder of the tubing segment. After this time, the speed of the pumps is diminished, so that the priming fluid and dialysate are not continually loaded with calcium, citrate, or potassium during the PRIME operation.

At the start of the PRIME mode, and during priming, tube 39 from the prime fluid container 42 is filled with priming fluid. During the first few cycles of operation, prime fluid is drawn into the dialyzer, and air is expelled. The computer is programmed to expect signals due to passage of air-fluid interfaces. After several minutes of rinsing of the dialyzer, bubbles should clear from the priming fluid. The clarity of this fluid is indicated both by the optical particle/flow monitors 60 and 61, and the interface detector 71.

During dialyzis, when air-fluid interfaces are detected by any of the detectors, the machine automatically enters the ALARM mode, and all clamps are closed. The speed of response is such that little air should pass the detector position, before the clamps are closed.

HEMOGLOBIN MONITOR

The presence of red cells (or, hemoglobin) in the dialysate fluid, during operation of the system, indicates a membrane leak in the dialyzer. Such leaks are rare in the plate dialyzers of high production quality. An optical monitor 74 exists on tube 37 coming from the dialyzer 33, to indicate the appearance of red cells during dialysis (should a blood leak occur).

The hemoglobin monitor (Hbg monitor) 74 is an optical system similar to the interface detectors. An LED emits light through the tube 45 which carries dialysate from the dialyzer. A phototransistor receives the light. The effect of ambient light is determined by the computer, during the time the LED is turned off. The output signal from the phototransistor is measured when the machine is first turned on, to determine this effect of tubing density. If no difference between the LED on and off signal is noted, the sensor is out of order and an appropriate alarm will be issued. The system will not run without an operational hemoglobin monitor. During PRIME, dialysate fluid enters tube 45 at a time when no blood contamination is possible. The output of the phototransistor indicates the "baseline" signal due to clear dialysate. During DIALYZE, the output voltage from the monitor is checked frequently by the computer. The presence of 1% red cells causes a decrease in output voltage of two fold. Shorter, large variations are caused by air bubbles leaving the dialyzer; however, these do not greatly affect the average output reading.

AMMONIUM MONITOR (NH4 MONITOR)

The NH4 monitor 75 (FIG. 5) is located on the outflow tube 49 of the sorbent column 48. The NH4 monitor is also an optical device, but it works to observe a paper strip rather than a tubing segment. The paper strip contains reacting chemicals which can react with ammonium, and change color in the process. An example of such chemical strip is the ammonium test strip available from Organon Teknika, which contains phthalate. The strip 78 is separated from the dialysate 79 by a gas permeable membrane 80 (such as, Teflo ® membrane, or CellGard ® polycarbonate membrane) so that none of the reactants can enter the dialysate (since none of them form gas or vapor). The tubing set 49 comes with a pre-attached strip and membrane. A 3/16 inch hole 99 in the tubing allows the dialysate to contact the gas permeable membrane. Tape 81 holds the strip and membrane in place. The strip 78 may be wetted with one drop of water, just before placing the strip holder into the sensor slot or it can also wet automatically in the first ½ hour of dialysis by water vapor transfer across the gas-permeable membrane. The sensor/tubing cover of the clear top helps to hold the tubing and chemical strip in place against the optical sensor.

The color development of the strip is monitored by a phototransistor 77. Strip 78 is illuminated by a red-wavelength LED 76, mounted at 60 degree angle to the tubing, as in FIG. 5. A phototransistor 82 monitors the output of the LED, and computer 66 adjusts the voltage to the LED, to give an adequate output from the phototransistor. This confirms the adequate operation of the LED. The output of the sensing phototransistor 77 indicates proper function of the phototransistor, and the proper position of the filter paper.

Figure 5:
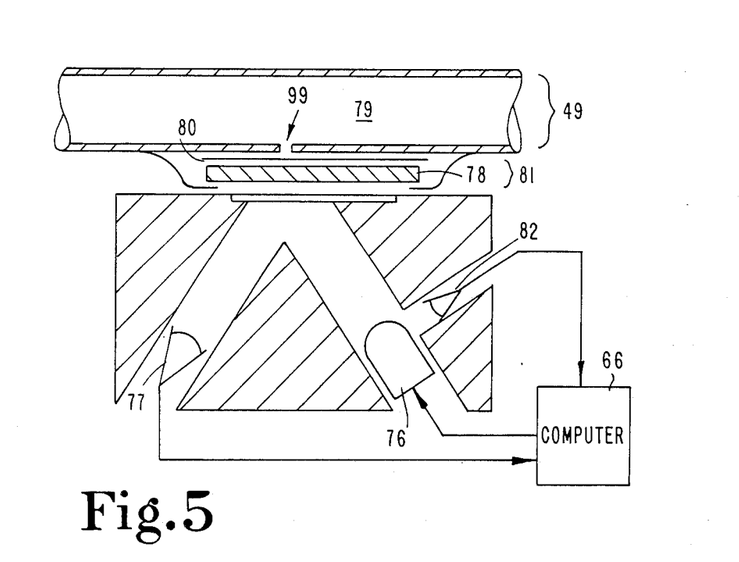
FIG. 5 is a schematic diagram of the ammonium monitor.

During the progress of dialysis, the voltage output of the phototransistor is monitored at one minute intervals. If saturation of the column occurs, ammonium levels in the outflow fluid rise continually over a 15 minute period, and the pH rises from about 6.5 to above 7.3. Ammonium (NH4) in the dialysis solution is associated with a certain amount of ammonia (NH3). At pH 7.3, the ratio of NH4 to NH3 is about 1000:1. Since the NH3 gas is highly diffusible, and since the reactants in the chemical strip react with NH3 to remove it from solution, there is rapid and continual passage of NH3 into strip 78. As the color of the strip darkens, the output of the phototransistor decreases. A fall in such voltage of 30% indicates significant ammonium appearance at the sensor, and saturation of the column. This causes the computer to place the machine in ALARM condition. As with the air-fluid interface and hemoglobin sensors intermittently turning off the LED allows for correction for ambient light.

The monitor is advantageous in that it can operate continuously and uses one strip to determine concentrations during entire dialysis. Further, leaching of potentially toxic chemicals to the dialysate via a gas permeable membrane is prevented.

SALT COMPONENTS OF THE ULTRAFILTRATE AND REINFUSATE RESERVOIRS 44 AND 50

To make setup of the system as simple as possible, the salts normally used for dialysate preparation are pre-measured and packed into the Disposables Cartridge 32. All that the patient needs to add is plain (potable) tap water.

A bag on the back of cartridge 32 is divided into two sections, the ultrafilitrate reservoir 43 and the potassium/citrate reservoir 50. Ultrafiltrate reservoir 43 contains, before dialysis, 360 mMoles of NaHCO3, and 40 mMoles of Na Citrate. After addition of 3 L tap water, and after 10 minutes of PRIME, the following dialysate concentrations result: sodium 90 meq/L, bicarbonate 72 meq/L, and citrate 8 mM/L (the majority of cirtrate being bound by the column). There is also 100 mg% glucose concentration, due to transfer of glucose across the dialyzer from the glucose-containing prime solution.

Reservoir 50 contains both potassium and hydrogen salts of citrate. To provide varying concentrations of potassium in the dialysate, there are cartridges of either 33%, 66% or 100% of the citrate as potassium. These are called "low", "medium", or "high" potassium cartridges. After addition of 300 ml tap water, the concentration of citrate in the reservoir becomes 1000 mM. During dialyzer operation, the resultant dialysate potassium concentration of the low K cartridge becomes 0.8-1 meq/l, the medium K cartridge is 1.0-2.2 meq/l, and the high K cartridge 2.8-3.2 meq/l.

In the last few minutes of PRIME, the pump 52 begins to transfer fluid to the ultrafiltrate reservoir 43. The volume of this reservoir is small during this time, so the potassium concentration quickly builds to its equilibrium concentration. Potassium is bound by the column, during passage through the column, but citrate is not (since the column has already been saturated with citrate). In the small volume of fluid in the ultrafiltrate reservoir 43 at this time, the potassium level quickly approaches its equilibrium level, and the citrate concentration of the ultrafiltrate reservoir is raised very little by the reinfusate.

During dialysis, the pump 52 operates to return a modest amount of citrate to the patient. The rate of citrate return to the patient is determined by the computer according to patient weight, and ranges from 0.9 mg/kg/min for patients of 40 kg dry weight, to 0.6 mg/kg/min for patients of 80 kg dry weight. Since the rate of citrate return is determined by the dry weight input of the patient, it is important that patients be encouraged to enter this value accurately.

Figure 6:
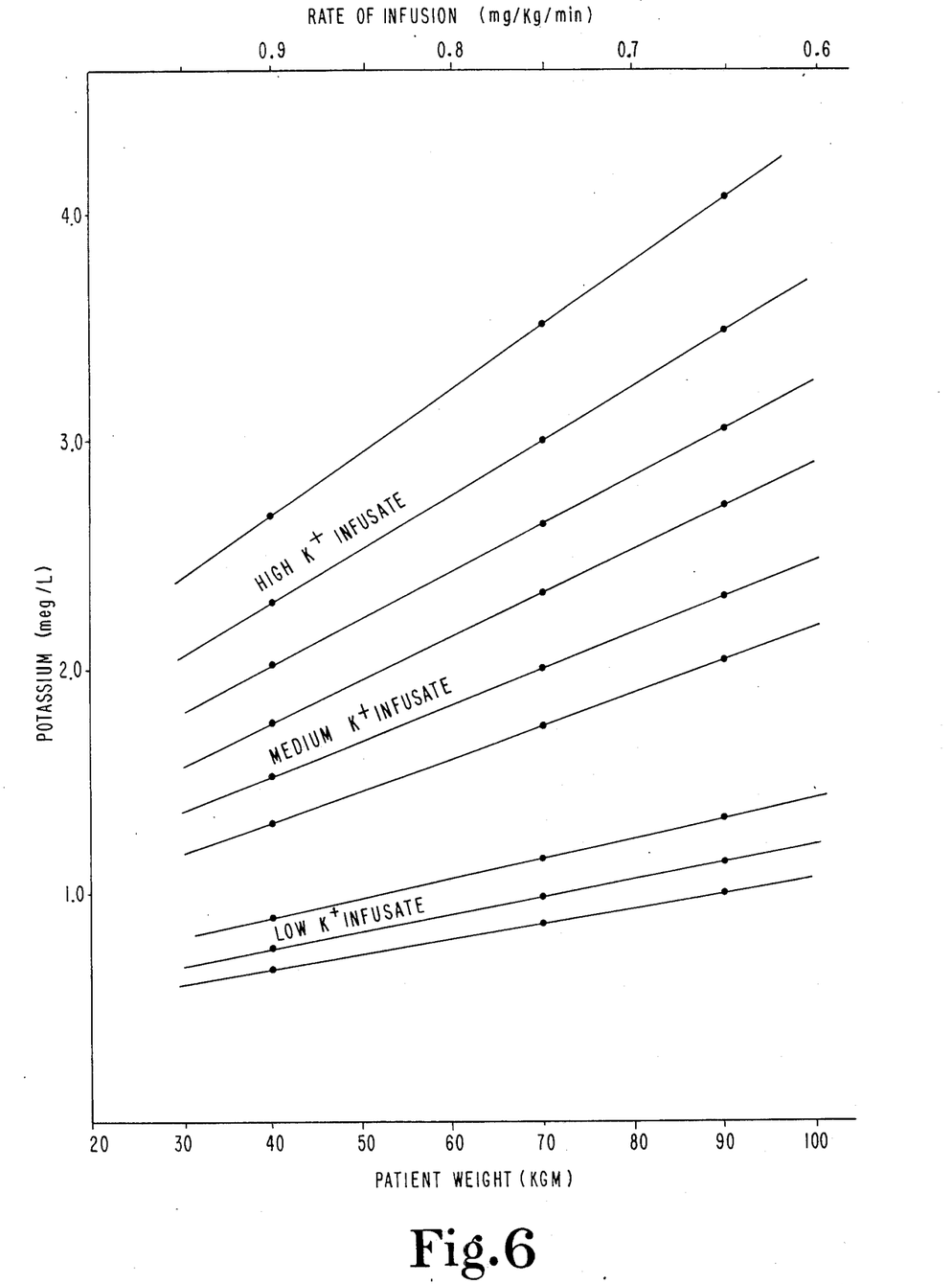
FIG. 6 is a graph depicting levels of potassium concentrations obtained in the dialysate with several infusates when the rate of infusion is adjusted to patient weight.

Since the potassium/citrate infusion rate is dependent upon patient weight, the equilibrium potassium concentration of the dialysate is also affected by this dry weight input. Also, as with any recirculating dialysate system, the concentration of the potassium is dependent somewhat on the rate of dialysate flow. In the system disclosed herein, variations in dialysate flow are used to optimize the blood flow rate. The effect of the variations in dialysate flow on potassium concentration is, in fact, rather minor. FIG. 6 indicates the equilibrium potassium concentration obtained for patients of varying dry weight, at varying dialysate flows. The lower line of re-infusate level indicates potassium concentrations at high dialysate flow (350 ml/min), and the upper line the potassium concentration at low dialysate flow (250 ml/min). This diagram is to be used by physicians to provide a Disposable Cartridge of appropriate potassium content for each patient.

In the early part of DIALYZE, the citrate concentration of the dialysate falls to a lower equilibrium level, from the 8 mM starting level. The return to the patient is then equal to the rate of transfer of citrate to the ultrafiltrate reservoir determined by pump 52. The outflow blood concentration depends upon the blood flow rate, of course.

The rate of return of citrate is less than the rate calculated to be safe in normal patients, and less than that used in dialysis anticoagulation experiments of Diederich and others. The reason that citrate is used in conjunction with the potassium in reservoir 50, rather than chloride, is threefold. First, citrate is metabolized by the liver, and chloride is not. Therefore, the total increase in anionic concentration of the patient is less, using citrate. Secondly, citrate is an effective buffer, similar in metabolic properties to lactate or acetate. In its metabolism by the liver, it removes hydrogen, thereby helping to correct uremic acidosis. Thirdly, citrate is an effective anticoagulant. The transfer of citrate across the dialyzer to the blood raises the activated clotting time very little. However, given the smooth blood pathway of Disposable Cartridge 32, lack of blood pump, and lack of drip chambers or screens, this effect of citrate may be sufficient to diminish heparin requirements significantly. As with standard hemodialysis, the exact heparin requirements should be determined during the patient training period.

CALCIUM CHLORIDE

The salts of the ultrafiltrate and reinfusate reservoirs do not contain calcium. The sorbent cartridge 48 removes all calcium from the fluid reaching it. Therefore, the dialysate of the disposables is essentially an 0 calcium "bath". The calcium transferred to dialysate from the blood during DIALYZE is removed by the column.

The reason for not providing calcium in the dialysate of the dialyzer is threefold. First, any calcium reaching the column tends to reduce the binding capacity for ammonium (since the ion exchangers of the column have a higher affinity for divalent calcium than for monovalent ions). Secondly, calcium would interfere with any beneficial anticoagulant effect of citrate. Finally, the provision of a separate calcium chloride container and pump allows variability in the rate of return of calcium, according to the needs of the patient.

A sterile 5% calcium chloride solution is provided in container 54 in Disposables Cartridge 32. The volume of this fluid is 250 ml. Pump 53 transfers this fluid to the outflow blood tube 40, at a point within the cartridge. The speed of operation of pump 53 is monitored through a tachometer attached to the motor. During PRIME, the flow is rapid for a period sufficient to fill tube 55. Pump 53 is then stopped, and restarted at the initiation of DIALYZE. The flow rate of the pump is then made proportional to the blood flow through the dialyzer, as measured by the optical flow/particle monitors.

During passage of blood through the dialyzer, approximately 40% of the blood calcium is removed. During CHECK/INPUT, one of the displays is the calcium/blood flow ratio. This ratio is, normally, 1 ml/400 ml of blood. This amount of calcium is calculated to return slightly more calcium than that removed in passage of blood through the dialyzer. The ratio of calcium return is adjustable upwards or downwards at this time, within limits of 1/200 to 1/900. The serum chemistries, and bone status of the patient may be used to determine the appropriate calcium return, as is done in any hemodialysis procedure.

THE SORBENT COLUMN

The Disposables Cartridge 32 contains a sorbent column 48 for dialysate purification. The cartridge is essentially similar to the HiSorb D-32 cartridge from Organon Teknika. The column has, within it, five separate layers of solid, particulate sorbents. The first layer is a thin layer of charcoal, designed to remove trace impurities from the tap water. The second layer contains immobilized urease. The urease serves to split urea, as in the following reaction:

$$urea \longrightarrow 2NH_4^+ + CO_3^=$$

The second layer contains zirconium phosphate. This substance contains a number of closely bound, but exchangeable ions. Sixty percent of the ions loaded are hydrogen, 40% sodium. In this layer, $NH_4^+$ is absorbed, in exchange for hydrogen or sodium. The ammonium sorption of this layer is sufficient for ammonium generated from 30 gm urea (at dialysate concentrations of 20 mg% urea). When this amount of ammonium has been absorbed, then ammonium will begin to pass through the zirconium phosphate layer.

The third layer of the column contains zirconium oxide. The function of this layer is to remove phosphate, in exchange for acetate. The fourth layer contains activated charcoal. The purpose of this layer is to absorb a variety of uremic substances such as uric acid, creatinine, phenols, etc.

The dialysate flow through the sorbent column is approximately 250 ml/min. Dialysate flow rate varies somewhat, as the computer adjusts the blood flow in and out of the dialyzer. In an alternate embodiment, column performance may be diminished, while overall dialysate flow is held constant, to maintain a resonable level of urea and remove $NH_4^+$ capacity of the column.

COMPUTER CONTROL

The dialysis system disclosed herein includes a computer 66 which is composed of two Intel 8751 computers 82 and 83 (FIG. 2) connected together. Computer 82 serves as a "spinal cord" receiving the input of various sensors, detectors and monitors and providing output commands for the motor drives of the various pumps 52, 53 and 56. The second computer 83 serves as a "brain" and receives commands from the control as operated by the patient and transfers such commands for operation of computer 82. The data concerning the dialysis is stored in a separate EEPROM for transfer through an RS232 port. This transfer might occur once per month or more frequently, if desired, to an office based computer. The entire dialysis machine rests on a base plate 84 (FIG. 1) through a scale mechanism. This scale 85 (FIG. 2) contains one or more sensitive strain gauges, to measure the weight gain of the machine during the entire hemodialysis period. The weight gain equals the ultrafiltration minus any fluid return from the various reinfusates. It thus should accurately measure the total fluid removal and weight loss by the patient. The scale 85 (FIG. 2) feeds information to computer 82. The scale is also sensitive enough to measure inflow and outflow volumes of the dialyzer. This can serve to confirm flow measurement of the optical flow monitor.

ULTRAFILTRATION CONTROL

Control of ultrafiltration is one important mechanism for minimizing intra-dialytic symptoms and preventing vascular collapse and shock. Without controlled ultrafiltration, it is necessary to predict fluid removal by the ultrafiltration coefficient of the dialyzer, and to set the transmembrane pressure gradient (TMP) accordingly. Dialyzer machines with controlled ultrafiltration capabilities have volumetric measuring or metering devices to set the net UFR. While such devices are generally accurate, they do not take into account the addition of fluid to the blood side from the priming solution and they add to the complexity and cost of present dialysis machines.

The ultrafiltration rate of the subject system is determined by the weight gain of the entire machine. Thus, reinfusion from the priming solution to the blood is automatically accounted for in the calculation of total weight removal from the patient. The rate of weight gain by the machine is equal to the weight loss from the patient. To adjust the rate of ultrafiltrate, computer 82 adjusts the volume in the dialyzer downward. This is accomplished by cutting off inflow at a slightly higher flow rate, thus decreasing the fill volume and transmembrane pressure of the dialyzer. To increase ultrafiltration rate, a lower flow rate is used for cutoff of inflow, thus increasing the volume and transmembrane pressure of the dialyzer.

The measurement of weight gain by the machine is through strain gauges mounted in the bottom of the machine. These may be attached to a supporting base plate 84, if desired. Addition of weight to the machine, as by setting objects on top of the machine during dialysis, can cause incorrect calculation of ultrafiltrate. Sudden increases of weight are sensed by the computer, and may set off an alarm indicating an inaccurate input. Sudden diminution of weight on the strain gauge indicates that the machine has been lifted. In this case, the computer merely continues the inflow and outflow cutoff points last calculated to provide proper ultrafiltration rate. Sudden increase in weight indicates that the machine has been set on a solid surface again. Re-adjustment of inflow and outflow cutoff points is then made, according to the presently measured weight increase of the machine.

GENERAL OPERATION

During initial setup, the patient makes the appropriate tubing connections within Disposable Cartridge 32, to the priming container 42 and calcium chloride container 54 as well as to dialyzer 33. The patient manually closes clamp 92. The priming process is initiated by pressing a button, and pump 56 begins to turn. Automatic closing of clamp 57 and tube 44 pulls priming fluid into the dialyzer. Closing of clamp 58 and tube 45 allows the dialyzer to expel fluid. Priming is confirmed and the monitors 60 and 61 indicate no air or particles and the interface detector 71 indicates no major bubbles. During this time, priming solution is taken from container 42, passed through the dialyzer and returned to container 42, in numerous cycles. Clamp 67 is kept open during this operation.

Upon completion of the priming mode, the patient places needle 41 into a fistula. The dialyze mode is initiated with the flow of blood into and out of the dialyzer controller entirely by the optical monitors 60 and 61. Pump 56 remains on at a slow rate. During inflow, clamp 57 is closed, clamp 58 is open and clamp 59 opens tube 45 and closes tube 44. Computer 82 monitors the increase of blood flow to make sure it exceeds 25 ml/min, then monitors the flow until it decreases to 25 mm/min which indicates the filling of the dialyzer. Clamp 58 is then closed, and clamp 57 opened, and clamp 59 closes tube 45 and opens tube 44. The computer monitors the increase of outflow past 25 ml/min and the deceleration of flow to 25 ml/min indicating appropriate emptying of the dialyzer. In successive cycles, the pump 56 is increased in speed until the average inflow and outflow velocities equal 300 ml/min.

This results in an average blood treatment of 150 ml/min.

The compliance curve of the dialyzer 33 and its UF coefficient have been programmed into the computer as has the relation of inflow rate to fill volume and transmembrane pressure. The computer selects the desired TMP for the desired ultrafiltration rate and translates this to a desired end point for inflow and outflow rate. The cycles of inflow and outflow are then adjusted according to these flow limits.

After these limits are set, the computer begins to measure the rate of weight gain of the machine (UF rate). If this rate is higher than the desired rate, slightly lower cutoff points are used to end inflow or outflow (5 ml/min flow rate difference). If the UF rate is less than desired, higher cutoff rates are chosen. This feedback adjustment continues throughout dialysis. Between each of these UF rate adjustments, the feedback algorithm to provide an average blood flow of 300 ml/min is still operative. If, as a result of lowering UF rate (and dialyzer fill volume), the average treatment rate falls, the pump speed of pump 56 is increased. If treatment rate becomes higher than 150 ml/min, the pump is slowed. In this way, it is possible to operate the dialyzer at either low or high UF rate, without greatly affecting the average blood treatment rate. The computer continues the dialysis mode until the desired (input) time is elapsed.

Upon completion of the dialysis, the patient presses a button to begin the rinsing cycle, and manually closes clamp 93. Clamp 67 opens automatically, and clamps 57 and 58 open and close as in the dialyze mode. The outflow blood flow monitor 61 indicates the effective rinsing of the dialyzer when its flow signal disappears.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

ALTERNATE EMBODIMENT

Alternately, the entire system can be used with a suspension of sorbents (urease, charcoal, cation exchanger such as calcium loaded zeolite or sodium-hydrogen loaded IRP, and anion exchanger) in place of column 48. The calcium-loaded zeolite is described in my U.S. patent application No. 482,210 now U.S. Pat. No. 4,581,141 and entitled DIALYSIS MATERIAL AND METHOD FOR REMOVING UREMIC SUBSTANCES IN AN ARTIFICIAL KIDNEY which is herewith incorpated by reference. The advantages include: low cost (no need to construct a column), improved clearance (diminished dialysate side chemical resistance), and smaller, simpler machine (no column pump necessary). All monitors work the same, except hemoglobin, which may be done with electrochemistry rather than optics.

Another further variation includes operating the system with heparin in place of CaCl$_2$ bottle as anticoagulant. Another alternative embodiment takes approximately 500 ml/min. dialysate flow to reach the goal blood flow of 150 ml/min. The Redy Column loses binding capacity, and has too high a head pressure at this flow. A short circuit of flow to the bag can bypass the column as shown by the dashed lines in FIG. 2. Thus, tube 47 is also connected to an auxiliary pump 90 located between pump 56 and column 48. Pump 90 in turn perfuses the column, connected to tube 91 emptying into the top of dialysate bag 43. Pump 90 is operable to force a portion of the dialysate flowing through tube 47 into tube 91 and then into bag 43 while flow is continuing from tube 47 into column 48. Pump 90 and tube 91 are shown in dashed lines since they are only incorporated into the alternate embodiment. All other features and components are identical with the embodiment previously described herein. One advantage is that column flow can be put high at beginning of dialysis, when blood-urea level falls, maintaining high dialysate urea to maintain high column bonding.

What is claimed is:

1. A single access dialysis instrument, comprising:
   a single catheter for transmission of body liquids to and from the body;
   a reciprocating dialyzer with dialyzer membranes and having body liquid side disposed within said dialyzer membranes including means for defining a body fluid inlet and a body fluid outlet connected to said catheter, said reciprocating dialyzer further having a dialysate side disposed outside said dialyzer membranes including means for defining a dialysate inlet and a dialysate outlet, said body liquid side and said dialysate side separated by said dialyzer membranes, said dialyzer membranes being compliantly formed to expand and contract in response to a corresponding change in pressure between said body liquid and said dialysate within said dialyzer;
   storage means connected to said dialysate inlet and said dialysate outlet for holding a supply of liquid including dialysate for use in said dialyzer; and,
   dialyzer control means for controlling the inflow and outflow of body liquid and dialysate to and from said dialyzer in a reciprocating cyclic fashion while maintaining said dialysate within said dialysate side of said dialyzer at a non-elevated pressure throughout the entire cycle of said dialyzer, said dialyzer control means further for maintaining a positive pressure gradient from said body liquid side to said dialysate side throughout the reciprocating cycle of said dialyzer.

2. The instrument of claim 1 wherein said dialyzer control means includes a dialysate pump communicating with said dialysate inlet and dialysate outlet of said dialyzer and operable to pump dialysate between said storage means and said dialysate side of said dialyzer.

3. The instrument of claim 2 wherein said dialyzer control means further includes a liquid flow control means having clamps associated with said body fluid inlet, said body fluid outlet, and said dialysate inlet to control flow there through, said liquid flow control means for controlling the flow of body liquid and dialysate to and from said dialyzer by operation of said clamps in association with said dialysate pump.

4. The instrument of claim 3 wherein said storage means is a disposable assembly including:
   a dialysate reservoir container for holding a quantity of water and defining an outflow port connected to said dialysate inlet and an inflow port connected to said dialysate outlet through said dialysate pump.

5. The instrument of claim 4 wherein said storage means further includes:
   a sorbent column to regenerate dialysate and for holding dialysate and body liquid side components for eventual disposal, said column being connected between and in fluid communication with said dialysate inlet and said dialysate outlet.

6. The instrument of claim 5 wherein said storage means further includes:
a reinfusate reservoir having chemicals therein being in fluid communication with said dialysate reservoir to supply said chemicals into said dialysate for the replenishment thereof.

7. The instrument of claim 6 and further comprising:
a body liquid infusate container connected between and to said catheter and said dialyzer.

8. The instrument of claim 1 and further comprising:
priming means connected to said body liquid side and in fluid communication with said dialyzer to hold a priming liquid being operable to provide liquid thereto to prime said dialyzer.

9. The instrument of claim 1 and further comprising:
monitoring means operably associated with said body fluid inlet and said body fluid outlet and having light detecting means operable to detect flow parameters of blood passing through said body fluid inlet and said body fluid outlet including detection of bubbles, clots and particles present therein.

10. The instrument of claim 9 and further comprising:
a container of a salt of citrate connected to said dialysate inlet.

11. The instrument of claim 10 and further comprising:
a disposable cartridge having said dialyzer, said storage means and said container of a salt of citrate mounted thereon; and,
a sorbent column mounted on said disposable cartridge and connected between said dialysate inlet and said dialysate outlet to remove impurities from said dialysate.

12. The instrument of claim 1 and further comprising:
weight measuring means associated with said dialyzer and said storage means for measuring changes in the weight of the machine due to withdrawal and return of body liquid through said catheter and due to ultrafiltration of fluid across said dialyzer.

13. The instrument of claim 1 and further comprising:
measurement means connected to said body liquid side of said dialyzer for instantaneously measuring body liquid flow into said dialyzer.

* * * * *